United States Patent [19]

Monnier et al.

[11] 4,105,409

[45] Aug. 8, 1978

[54] METHOD AND REAGENT FOR DETERMINING THE ETHYL ALCOHOL CONTENT OF A GAS

[75] Inventors: Denys Monnier, Chênes-Bougeries; Pierre Bolle, Genèva, both of Switzerland

[73] Assignees: Lucien Etzlinger, Geneva; Carl Wilhelm Koelker, Baar; Claus H. Grossman, Kusnacht; Multi-Marketing Services AG., Basel, all of Switzerland

[21] Appl. No.: 792,168

[22] Filed: Apr. 29, 1977

[30] Foreign Application Priority Data

May 6, 1976 [CH] Switzerland ..................... 5711/76

[51] Int. Cl.$^2$ ..................... G01N 31/22; G01N 33/16
[52] U.S. Cl. ..................... 23/232 R; 252/408
[58] Field of Search ..................... 23/232 R, 254 R; 252/408

[56] References Cited

U.S. PATENT DOCUMENTS

| 2,939,768 | 6/1960 | Grosskopf et al. | 23/232 R |
| 3,437,449 | 4/1969 | Luckey | 23/232 R X |

*Primary Examiner*—Robert M. Reese
*Attorney, Agent, or Firm*—Ladas, Parry, Von Gehr, Goldsmith & Deschamps

[57] ABSTRACT

The invention concerns a reagent for determining the ethyl alcohol content of a gas, particularly human breath, by means of a color reaction. This reagent consists of a mixture of iodine pentoxide, a colorless metal nitrate or concentrated nitric acid, and 75-98% sulphuric acid, the original white color of the reagent changing to pink, brown or black depending on the ethyl alcohol content of the gas. In a preferred embodiment of the invention, the reagent is placed in a tube for use in connection with drunken driving.

7 Claims, No Drawings

METHOD AND REAGENT FOR DETERMINING THE ETHYL ALCOHOL CONTENT OF A GAS

The present invention relates to a novel reagent for determining the ethyl alcohol content of a gas by means of a color reaction, in particular for determining the ethyl alcohol content of a human breath sample.

It has been known for a long time that the ethyl alcohol content of human breath can be determined by means of a color reaction based on the reduction of a bichromate solution by the ethyl alcohol, the original yellow color of the solution changing to green.

This method was used some time ago by police forces in many lands for the detection and prosecution of drunken drivers. For this purpose, the bichromate reagent was contained in a glass tube through which a suspected driver had to exhale. This cheap and simple form of the method was however abandoned since it proved inexact and unreliable. It was above all the judgement of the color change from yellow to green which often gave considerable difficulty; the color change was not very easy to recognise owing to the pale colors resulting from the amount and concentration of bichromate reagent in the tube. If in addition the alcohol test was carried out at night in artificial light, the recognition of the color change was all the more problematic.

When this form was discarded, the bichromate method was further developed and improved by including a photometer to an exact, quantitative method. The exactness and reliability thus obtained must however be weighed against the greater complexity of the method, i.e. by the correspondingly greater susceptibility to failure and correspondingly higher price of the equipment. Owing to its relatively high price, such equipment can understandably be made available to the police only on a restricted scale.

Hitherto, there has therefore been no method for determining the ethyl alcohol content of the breath which is not only so simple and cheap that it is suitable for the routine investigation of drivers but also more reliable than the originally used bichromate method.

Such a method, based on the novel reagent of the invention, has now been discovered. The reagent consists of an intimate mixture of (1) iodine pentoxide, (2) a colorless metal nitrate or concentrated nitric acid and (3) 75 to 98% (wt./wt.) sulphuric acid, the original white color of the reagent changing to pink, brown or black depending on the proportion of ethyl alcohol added.

The preferred sulphuric acid concentration lies between 80 and 90% (wt./wt.).

Sodium nitrate, potassium nitrate or cerium(III) nitrate hexahydrate, $Ce(NO_3)_3.6 H_2O$, is generally used as the colorless metal nitrate.

The reagent is conveniently adsorbed on a solid, inert, porous carrier and used in this form. Suitable carriers are for instance silica gel, kieselguhr (diatomaceous earth), fuller's earth, zeolites and aluminium oxide. Silica gel is preferred, particularly one with an average grain size of 0.2 to 0.5 mm (equivalent to 35 to 70 mesh according to ASTM), e.g. "Kieselgel 100" made by Merck AG, Darmstadt (W. Germany). The breath to be investigated is exhaled through the porous reagent mass.

In a preferred embodiment of the invention, the reagent on 100 g of silica gel contains (1) 10 to 50 but preferably 10 to 20 g of iodine pentoxide, (2) 5 to 25 but preferably 5 to 15 g of metal nitrate or 3 to 10 but preferably 4 to 5 ml of concentrated nitric acid and (3) 50 to 120 but preferably 80 to 100 ml of 80 to 98% (wt./wt.) sulphuric acid.

Instead of being adsorbed on a solid carrier, the reagent may also be used as a solution, preferably in moderately concentrated sulphuric acid. 10 to 50%, in particular 20 to 30%, e.g. 25% (wt./wt.) sulphuric acid is suitable for this purpose. The breath to be investigated is passed through this solution.

When pure, the reagent is white. If it contains cerium(III) nitrate as the metal nitrate and this cerium salt is contaminated with cerium(IV) nitrate, the reagent may have a slight yellowish tinge. Care should therefore be taken that only pure products are used in the preparation of the reagent.

The addition of ethyl alcohol leads almost immediately to a redox reaction producing elementary iodine which separates out. The separated iodine remains suspended or partly dissolved in the concentrated sulphuric acid. A strong coloration is produced which — depending on the iodine, i.e. the ethyl alcohol, concentration — is first pink, then brown or violet-brown and finally black. It should be mentioned that the redox reaction proceeds without the mixture of reagent and ethyl alcohol having to be warmed. The heat released as a result of the dilution of the concentrated sulphuric acid by the water vapour in the exhaled air warms up the reagent, thus accelerating the reaction. In addition, the metal nitrate or concentrated nitric acid acts as a catalyst to ensure that the reaction proceeds rapidly.

Although the color change is perfectly clear if a reagent containing concentrated nitric acid or sodium or potassium nitrate is used, it is more conspicuous and take place practically instantaneously when cerium(III) nitrate is employed. The latter nitrate is therefore the preferred metal nitrate in the reagent of the invention.

A color change from white to dark colors such as brown or black with the novel reagent can naturally be detected by eye much more readily than a color change from light yellow to light green as was the case with the original form of the prior art bichromate reagent. This represents a decisive advantage of the novel reagent. In addition, the indicator is the oxidising agent itself (iodine pentoxide). This represents the further advantage of greater simplicity compared with other reagents or systems requiring the addition of an additional component as the indicator.

As already mentioned, the reagent is eminently suitable, especially in the embodiment described below, for determining the ethyl alcohol content of human breath. It can however also be used for determining the ethyl alcohol content of other gases such as normal air or the air in a wine cellar or distillation room etc., provided of course that these gases or gas mixtures contain no reducing agents other than ethyl alcohol.

The embodiment preferred for practical use contains cerium(III) nitrate hexahydrate as the metal nitrate, is adsorbed on silica gel and is in granular form. Care should be taken during manufacture to ensure not only that the starting materials are pure but also that the mixture is as homogeneous as possible. For this reason, the iodine pentoxide and cerium(III) nitrate hexahydrate should not be prepared until shortly before mixing in order to avoid the absorption of any moisture. In addition, the silica gel should be impregnated with the concentrated sulphuric acid, the iodine pentoxide and cerium(III) nitrate mixed thoroughly together and this mixture mixed little by little into the impregnated silica gel while the latter still has a pasty consistency. Finally, the reagent thus prepared is homogenized and reduced in size in a shaking machine until it is quite dry and in granular form.

In this form it is placed in a thin tube through which the breath to be investigated is blown. The tube is made of a transparent material, e.g. glass or a plastic, and has a length of 5 cm and a suitable internal diameter, e.g. 3 mm. For a given volume of exhaled air with a given ethyl alcohol content, the amount of reagent, i.e. the length and breadth of the reagent mass in the test tube, can be adjusted so that the intensity of the color — pink/brown/black — and the length of the coloration gives the ethyl alcohol content in mg per 100 ml. For a given chemical composition of the reagent and concentration of its components, the sensitivity of such a breath test depends in fact on the inner diameter of the tube, the length of the reagent mass and how tightly packed the reagent mass is on the one hand and on the amount of alcohol in the breath on the other. The sensitivity of the reagent can also be varied at will by adding alum or water. Hence the above parameters can be adjusted so that the color reaction occurs when the alcohol content of the blood of the person exhaling through the tube is e.g. 30 mg per 100 ml, 50 mg per 100 ml or 80 mg per 100 ml. Thus appropriate adjustment of the amounts, dimensions and proportions allows any degree of drunkenness to be ascertained.

The reagent of the invention and the determination method based on it therefore make available to the police force a simple, cheap and rapid means of making routine checks on whether a driver is drunk or sober, i.e. exactly the method which has been needed for so long. The degree of drunkenness is then confirmed by the photometric bichromate method or by taking and analyzing a blood sample only for those drivers whose blood alcohol content is shown by the novel reagent to be over the permitted level.

In the form of the tube described above, the reagent can also be used in another equally worthwhile way, viz. to enable the driver to check his own condition before he gets into his car. For this purpose, the breath test tubes could be made available at the exits of restaurants and other public premises such as filling stations and motorway service areas.

In the following examples, all parts are by weight unless stated otherwise.

EXAMPLE 1

100 parts of "Kieselgel 100" silica gel made by Merck AG, previously well dried at 110° C, 184 parts (= 100 parts by vol.) of 98% sulphuric acid, 15 parts of iodine pentoxide and 5 parts of cerium(III) nitrate hexahydrate, $Ce(NO_3)_3.6 H_2O$, are used.

The silica gel is slowly impregnated, with stirring, with the sulphuric acid to give a completely homogeneous mixture. The finely ground iodine pentoxide and the finely ground cerium(III) nitrate hexahydrate are mixed well together and this mixture added gradually to the impregnated silica gel while the latter is still pasty and in any case before it has dried out completely. The resulting product is then rigorously mixed and reduced in size in a shaking machine until a fine, solid granulate material is formed.

A given quantity of the granular material is placed in 5 cm long tubes and compacted to fill a length of 1 cm in the middle of the tube. The reagent mass is held in place between two air-permeable supports. Suitable supports are sintered glass discs, plugs of glass wool or rectangular teflon rods. Both ends of the tube are then sealed by melting. Care should be taken that the tube and supports are clean and that the tube is not sealed too close to the reagent since the reagent becomes colored and thus unusable under the influence of heat.

EXAMPLE 2

The same procedure is followed as in example 1, but using 100 g of "Kieselgel 100" silica gel, 184 g of 98% sulphuric acid, 10 g of iodine pentoxide and 5 g of cerium(III) nitrate hexahydrate.

EXAMPLE 3

The same procedure is followed as in example 1, but using 100 g of "Kieselgel 100" silica gel, 184 g of 98% sulphuric acid, 15 g of iodine pentoxide and 5 ml of concentrated nitric acid (spec. gravity 1.38 to 1.41).

EXAMPLE 4

The same procedure is followed as in example 1, but using 100 g of "Kieselgel 100" silica gel, 184 g of 98% sulphuric acid, 6 g of water, 10 g of iodine pentoxide and 6 g of cerium(III) nitrate hexahydrate.

EXAMPLE 5

The same procedure is followed as in example 1, but using 100 g of "Kieselgel 100" silica gel, 184 g of 98% sulphuric acid, 6 g of water, 10 g of iodine pentoxide and 8 g of potassium nitrate.

EXAMPLE 6

The same procedure is followed as in example 1, but using 100 g of "Kieselgel 100" silica gel, 110 ml of 80% sulphuric acid, 15 g of iodine pentoxide and 5 g of cerium(III) nitrate hexahydrate.

What is claimed is:

1. A reagent for determining the ethyl alcohol content of a gas by means of a color reaction, said reagent consisting of an intimate mixture of (1) iodine pentoxide, (2) a colorless metal nitrate or concentrated nitric acid and (3) 75 to 98% (wt./wt.) sulphuric acid, the original white color of said reagent changing to pink, brown or black depending on the ethyl alcohol content of the gas.

2. The reagent of claim 1 wherein said metal nitrate is sodium nitrate, potassium nitrate or cerium(III) nitrate hexahydrate.

3. The reagent of claim 1 adsorbed on a solid, inert, porous carrier.

4. The reagent of claim 3 wherein said carrier consists of a silica gel with an average grain size of 0.2 to 0.5 mm, equivalent to 35 to 70 mesh (ASTM).

5. The reagent of claim 3 wherein said reagent on 100 g silica gel contains (1) 10 to 50 g of iodine pentoxide, (2) 5 to 25 g of metal nitrate or 3 to 10 ml of concentrated nitric acid and (3) 50 to 120 ml of 80 to 98% (wt./wt.) sulphuric acid.

6. The reagent of claim 5 wherein said reagent is granular in form and contained in a tube made of a transparent material.

7. A method of determining the ethyl alcohol content of human breath comprising contacting the human breath with the reagent of claim 1.

* * * * *